United States Patent [19]

Wierenga

[11] Patent Number: 5,035,149

[45] Date of Patent: Jul. 30, 1991

[54] SOIL SOLUTION SAMPLER

[76] Inventor: Peter J. Wierenga, 7500 Calle Sin Desengano, Tucson, Ariz. 85718

[21] Appl. No.: 458,999

[22] Filed: Dec. 29, 1989

[51] Int. Cl.⁵ .......................... G01N 1/14; E21B 49/08
[52] U.S. Cl. ................... 73/863.23; 73/864.35; 73/864.73; 175/59
[58] Field of Search ........... 73/863.23, 863.24, 863.25, 73/864.73, 864.74, 864.34, 864.35, 73, 864.33; 175/59

[56] References Cited

U.S. PATENT DOCUMENTS

| | | | |
|---|---|---|---|
| 2,004,194 | 6/1935 | Lacy-Mulhall | 73/863.23 X |
| 2,214,551 | 9/1940 | Edwards | 175/59 |
| 2,386,832 | 10/1945 | Zaikowsky et al. | 73/864.73 X |
| 3,084,553 | 4/1963 | Lullinon et al. | 73/864.74 X |
| 3,188,563 | 6/1965 | Jameson | 73/73 X |
| 3,198,265 | 8/1965 | Voelkerding | 73/864.74 X |
| 3,521,715 | 7/1970 | Kratein | 175/59 X |
| 4,047,437 | 9/1977 | Brooks | 73/863.23 |
| 4,501,161 | 2/1985 | Endo et al. | 73/863.25 X |
| 4,745,801 | 5/1988 | Luzier | 73/863.24 X |
| 4,759,227 | 7/1988 | Timmons | 73/863.23 |

FOREIGN PATENT DOCUMENTS

| | | | |
|---|---|---|---|
| 795533 | 10/1968 | Canada | 73/863.23 |
| 438794 | 12/1926 | Fed. Rep. of Germany | 73/864.74 |
| 2279091 | 2/1976 | France | 73/863.23 |
| 1496713 | 7/1989 | U.S.S.R. | 73/73 |
| 979984 | 1/1965 | United Kingdom | 73/864.33 |

OTHER PUBLICATIONS

"A Probe Method for Soil Water Sampling and Subsurface Measurements"; *Water Resources Research*; vol. 17, NO. 6, pp. 1731-1736; Dec. 1981; W. D. Harrison et al.
"A Stainless Steel Soil Solution Sampler for Monitoring Pesticides in the Vadose Zone"; *Soil Sci. Soc. Am. J.*, vol. 50, pp. 263-265, pub. 1987; by C. N. Smith et al.

Primary Examiner—Tom Noland
Attorney, Agent, or Firm—Ross, Howison, Clapp & Korn

[57] ABSTRACT

A soil solution sampler is constructed of stainless steel by joining a porous stainless steel tube to a non-porous stainless steel tube to form a soil solution receptacle. Air and sample transfer conduits extend from the earth's surface into the receptacle. By drawing a vacuum on the air conduit, soil solution is drawn through the porous wall into the buried sampler. After collection, the sample is transferred to the surface through the sample transfer conduit by applying positive air pressure to the air conduit. In one embodiment, a divider wall having a port and one-way check valve separates the receptacle into an upper soil solution entry chamber having a porous wall, and a lower collection chamber into which the air and sample transfer conduits extend.

9 Claims, 1 Drawing Sheet

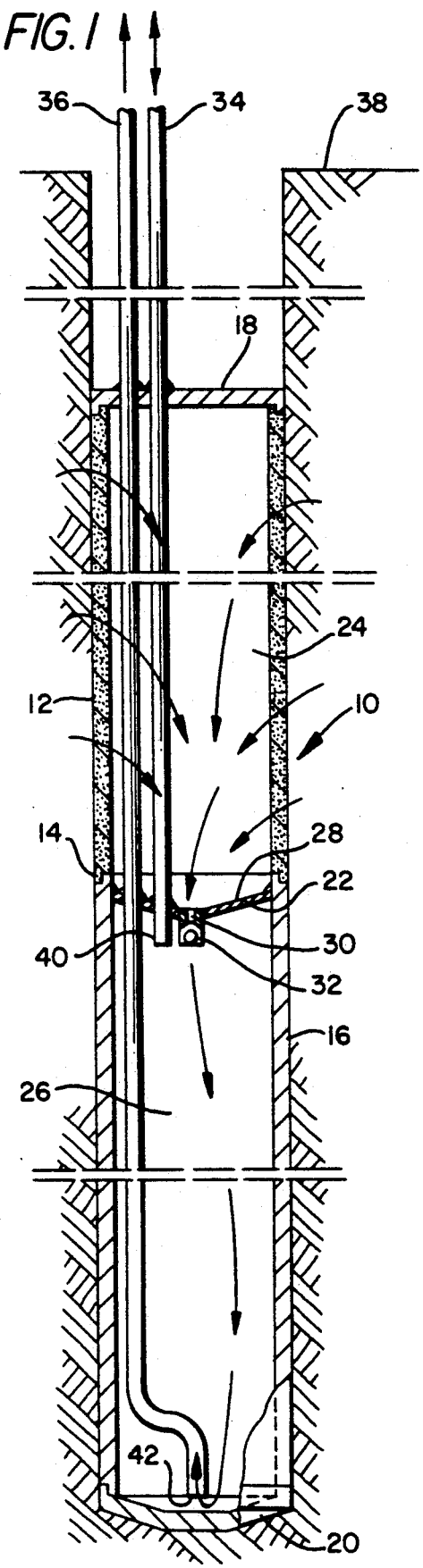
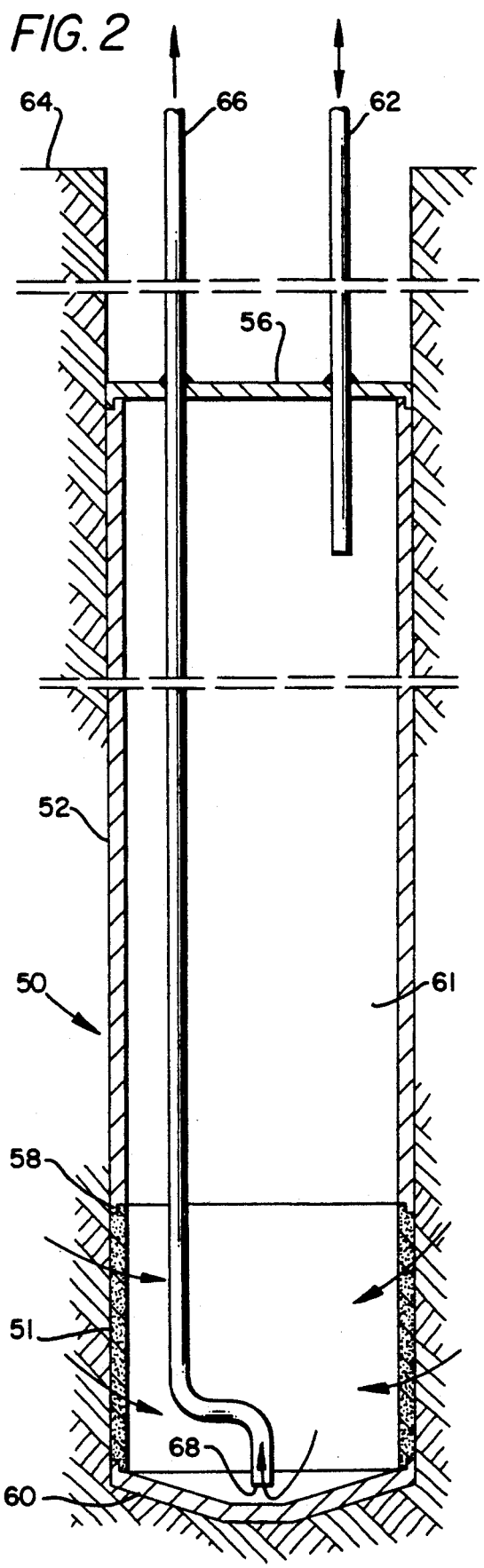

SOIL SOLUTION SAMPLER

FIELD OF THE INVENTION

This invention relates to soil solution samplers, sometimes referred to as lysimeters, and more particularly, to devices of this type which are buried in the earth to draw by vacuum a soil solution into the sampler through porous walls, and to transfer the solution sample to the surface by positive air pressure or vacuum.

BACKGROUND OF THE INVENTION

Systems for the collection and analysis of soil solutions for various agricultural and environmental studies have been extensively developed over a number of decades. Soil solutions are generally defined as the interstitial water in the soil, together with solutes and dissolved gases. The literature contains extensive disclosures of devices, sometimes called lysimeters, for the in situ collection of representative soil solution samples. One type, sometimes called a suction lysimeter, consists of a receptacle to be implanted in the earth. An air conduit extends from the earth's surface into the receptacle. By drawing a vacuum on the air conduit, soil solution is drawn in from the surrounding soil through the porous walls and collected in the receptacle. A separate conduit for transferring the soil solution sample brings the sample to the surface when positive air pressure is applied to the receptacle through the air conduit. Alternatively, transfer to the surface may be effected by vacuum if from a relatively shallow sampler, although this is less desirable because of the danger of volatilizing components of the sample. This invention is directed to soil solution samplers of this general type.

The predominant type of suction lysimeter in use is one employing a porous ceramic cup adhered to the bottom of a closed plastic tube, typically by an adhesive. Concern over the accuracy and representativeness of samples collected with this type of sampler has been widely reported. The possibilities of sample contamination with respect to certain component analyses exist with the use of the standard suction lysimeter. Potential contamination includes the introduction of extraneous components to the sample as well as the tendency to remove constituents from the soil solution, and thus distort the analytical results derived from the sample. For example, one concern is the ability of the porous ceramic cup to absorb certain constituents of the soil solution. Contamination may also occur by leaching of anions from the ceramic material. Moreover, adhesives used in assembling the device may contribute contaminants to the sample.

As a result of these concerns, various other materials for the porous medium through which the soil solution will pass into the receptacle have been proposed. Such alternate materials include, for example, fritted glass, alundum, sintered glass, Teflon ® and hollow cellulose fibers. An extensive review of lysimeter types and methodology as described in the technical literature may be found in a recent article entitled "Review of Solution Samplers" by M. Iggy Lataor, published in *Water Resources Research*. May 1988, Vo. 24, No. 5, pages 727-733.

The concept of this invention encompasses a soil solution sampler which addresses many of the concerns of the art concerning contamination, and which is readily fabricated without the use of adhesives. Samplers may be constructed in accordance with one aspect of the invention so as to be usable in very deep testing locations.

The improved strength of samplers constructed in accordance with the invention is a substantial advantage. Loss through breakage is reduced, particularly in deep soil placements. Installation may be effected in some soils by pressing the sampler into the ground, without the necessity of pre-drilled holes which increase installation cost.

SUMMARY OF THE INVENTION

In accordance with the invention, there may be provided a soil solution sampler having a receptacle comprised of a first tube formed from porous stainless steel to permit flow of solution through its wall, and a second tube formed of non-porous stainless steel joined to the end of the first tube. An air conduit for applying a vacuum to the interior of the receptacle at first times and for applying positive pressure to the interior of the receptacle at second times is provided extending into the receptacle from the earth's surface. A sample transfer conduit for conveying samples from the receptacle to the surface at such second times is also provided.

In another respect, the invention contemplates a suction lysimeter which comprises a stainless steel collection receptacle having at least a portion of its wall formed from porous stainless steel adapted to transmit soil solution therethrough into the receptacle.

In a specific preferred form of the invention, a soil sampler receptacle is divided into a soil solution entry chamber having a cap closing its upper end and having a porous wall permitting entry of the soil solution, and a non-porous collection chamber having one end secured below the end of the entry chamber opposite the entry chamber cap. A non-porous divider separates the entry chamber and the collection chamber and has a port for fluid communication between the two chambers. The port includes a one way check valve permitting flow of soil solution only in one direction, from the entry chamber to the collection chamber. The sampler includes a sample transfer conduit extending through the chamber cap, the entry chamber and the entry divider into the bottom of the collection chamber, and an air-conduit extending through the cap, the entry chamber and the divider into the collection chamber.

In one of its broad aspects, the invention contemplates improvement to standard suction lysimeters by providing a porous stainless steel tube as the sole permeable portion of the lysimeter receptacle wall for permitting transfer of soil solution into the receptacle, and for increasing the mechanical strength of the device.

BRIEF DESCRIPTION OF THE DRAWINGS

A more complete understanding of the invention may be obtained by reference to the following detailed description when taken in conjunction with the accompanying drawings, in which:

FIG. 1 is a partial central longitudinal cross-section of a soil solution sampler embodying a preferred form of the invention; and FIG. 2 is a similar view of a modified form of the invention.

DETAILED DESCRIPTION OF THE INVENTION

An all stainless steel soil solution sampler constructed in accordance with a preferred form of the invention is indicated generally by reference numeral 10 in FIG. 1. The soil sampler 10 is shown positioned in the earth. After placement, the space above the sampler is normally backfilled with soil (not shown) The upper portion of sampler 10 is formed by a porous stainless steel tube 12 which is joined at its open lower end 14 to a non-porous stainless steel tube 16. At its upper end, porous stainless steel tube 12 is closed by non-porous stainless steel entry chamber cap 18. Tube 16 is closed at its lower end by wall 20 and at its upper end by non-porous stainless steel divider 22. Wall 20 may take the form of a well-point or other conical or pointed configuration to facilitate placement of the sampler without the use of a pre-drilled hole.

Divider 22 at the top of tube 16 separates the receptacle of sampler 10 into an upper soil solution entry chamber 24 and a lower collection chamber 26. Divider 22 has a generally conical upper surface 28 confronting entry chamber 24 so that the floor of entry chamber 24 converges downwardly to a lowermost central area where a port 30 is formed for permitting flow of soil solution downwardly from the entry chamber 24 into the collection chamber 26. Port 30 is provided with a one-way check valve 32 which permits such flow, but prevents passage of fluid upwardly through port 30.

All of the parts of sampler 10 may be secured together by welding without the necessity of adhesives. The wall thickness of tubes 12 and 16 are preferably on the order of about 2 mm. Representative dimensions for the sampler are a tube outside diameter of approximately 32 mm. and an overall height of 35 cm., with the upper tube 12 being approximately 20 cm. and the lower tube 16 being approximately 16 cm. The dimensions may be varied to satisfy the demands of particular applications. The porous stainless steel forming the tube 12 should be of connected porosity sufficient to permit migration of soil solution from the surrounding earth through the tube wall into entry chamber 24, and have a bubbling pressure equivalent to at least about 200 cm. of water. A suitable porous stainless steel is available from Andreas Co., 17 College Street, Suite D, Greenville, S.C., under the designation "Poral Inox".

Sampler 10 is completed by air conduit 34 and sample transfer conduit 36 which extend upwardly to the earth's surface from sampler 10. Air conduit 34 extends through apertures in entry chamber cap 18 and divider 22 so that its lower end 40 is positioned in the upper portion of collection chamber 26. Soil transfer conduit 36 likewise extends through apertures in the entry chamber cap 18 and divider 22 so that its lower end 42 is adjacent the bottom of collection chamber 26.

When installed in the operating position shown in FIG. 1, sampler 10 may be used periodically to extract soil solution samples and transfer them to the surface for chemical analysis. The collection of samples is conducted at selected first times by applying a vacuum to the upper end of air conduit 34, while keeping the upper end of conduit 36 closed. The withdrawal of air from sampler 10 withdraws soil solution from the surrounding earth structure through the porous stainless steel wall of tube 12 into entry chamber 24 and thence downwardly through port 30 into collection chamber 26. At a time subsequent to collection of the sample, the sample may be transferred to the surface through sample transfer conduit 36 by applying positive air pressure to collection chamber 26 through conduit 34.

The dual chamber configuration of sampler 10 permits transfer even where a sampler has been placed at a substantial depth beneath the earth's surface. Divider 22 and one way check valve 32 cooperate to prevent the substantial air pressures through air pressure conduit 34 needed to transfer the sample from a great depth, from causing loss of sample outwardly through the porous surface of tube 12. This configuration permits sampling of soil solution at much more substantial depths than conventional lysimeters, while minimizing volatilization of organics from the soil solution by excessive vacuum.

It will also be appreciated that the sampler construction in accordance with this invention enables optimal integrity of the soil solution sample to be maintained. Stainless steel, which comprises substantially all of the makeup of sampler 10, does not interact with the soil solution to interfere with the chemical analysis of the solution. The sampler 10 has a very simple fabrication and assembly, and requires no use of adhesives. The all stainless steel construction renders the device rugged, reducing breakage losses and permitting placment in certain soils without predrilled holes.

An even simpler form of soil solution sampler 50 constructed in accordance with the invention is illustrated in FIG. 2. Sampler 50 does not utilize the two chamber sampler configuration and thus is less expensive, although it is less appropriate for use in very deep locations. Sampler 50 is formed by a joining of a non-porous stainless steel tube 52 and a porous stainless steel tube 54. Non-porous stainless steel tube 52 is provided with an upper cap 56, and is welded to tube 54 at its open lower end 58. Porous stainless steel tube 54 has closed lower end 60 so that the two tubes form a receptacle 61. Both tubes 52 and 54 may be formed from materials similar in type and thickness to the tubes of sampler 10. Air conduit 62 extends from the earth's surface 64 through the cap 56 into the upper portion of receptacle 61. Transfer conduit 66 likewise extends through cap 56 into the sampler 50, and has lower end 68 positioned adjacent the bottom of receptacle 61. All of the component portions of sampler 50 may be joined by welding, and the use of adhesives is not required. Typical dimensions for sampler 50 would be a 2 inch diameter with an approximate 14 inch height. The lower porous wall tube 54 may be approximately 2 inches long and the tube 52 approximately 12 inches.

An alternative to the materials of the sampler of FIG. 2 is also possible. Both tubes 52 and 54 may be formed from a single porous stainless steel tube. In this event, it is not necessary to weld pieces together to form the vertical walls of the collection receptacle. It is even possible to form the closed end wall 60 from porous stainless steel.

The operation of sampler 50 is similar to that described for the embodiment shown in FIG. 1. Sample is collected by drawing a vacuum on air conduit 62, causing soil solution to be drawn through the porous wall of the tube 54 into the sampler. At a subsequent time, the sample may be transferred to the surface by application of positive pressure to conduit 62, causing the sample to rise through transfer conduit 66 for acquisition and analysis. Less desirably, because of the danger of volatilization, one could draw the soil to the surface from shallow samplers simply by applying vacuum to conduit 66 while keeping conduit 62 closed.

This embodiment of the invention permits the construction of a sampler entirely from stainless steel components, minimizing sample contamination or distortion. The sampler is of simple and rugged construction and may be readily welded without the use of adhesives.

Although the preferred embodiments have been described in detail, it should be understood that various changes, substitutions and alterations can be made therein without departing from the spirit and scope of the invention as defined by the appended claims.

I claim:

1. In a suction lysimeter, a soil solution sampler comprising:
   a soil solution receptacle comprised of a first tube formed from porous stainless steel having a bubbling pressure of at least about 200 cm. $H_2O$ to permit drawing of soil solution into the sampler through a porous stainless steel wall thereof, and a second tube formed from non-porous stainless steel, joined to an end of the first tube; and
   a sample transfer conduit extending into the receptacle for conveying sample from the sampler.

2. The device of claim 1, further comprising an air conduit extending into the receptacle, for applying a vacuum to the interior of the receptacle at first times to draw soil solution into the receptacle through the wall of the first tube, and for applying positive air pressure to the interior of the receptacle at second times to extract the collected sample through the sample transfer conduit.

3. A soil solution sampler for a suction lysimeter comprising:
   a stainless steel collection receptacle having at least a portion of a wall thereof formed from porous stainless steel having a bubbling pressure of at least about 200 cm. $H_2O$ adapted to transmit soil solution therethrough into the receptacle; and
   a sample transfer conduit extending from a lower portion of the interior of the receptacle to the exterior of the receptacle.

4. The sampler of claim 3, further comprising an air conduit extending into the receptacle, for applying a vacuum to the interior of the receptacle at first times to draw soil solution into the receptacle through the wall of the first tube, and for applying positive air pressure to the interior of the receptacle at second times to extract the collected sample through the sample transfer conduit.

5. The sampler of claim 4, wherein all portions of the device, including the sample transfer and air conduits are formed from stainless steel, and the sample is constructed by welding and not by use of adhesives.

6. The sampler of claim 4, wherein the porous stainless steel portion of the receptacle wall is spaced from a bottom of the receptacle, and further comprising:
   a stainless steel divider forming upper and lower chambers in the receptacle so that the porous stainless steel portion of the receptacle wall is adjacent solely to the upper chamber and the lower chamber is defined by non-porous stainless steel walls; and the ends of the sample transfer and air conduits are in the lower chamber;
   a port in the divider; and
   a one-way check valve in the port permitting flow of soil solution only from the upper chamber to the lower chamber.

7. The sampler of claim 6, wherein an upper surface of the divider confronts the upper chamber and is conical so that is converges to the port at the lowest point of the upper chamber.

8. In a soil solution sampler having a receptacle for receiving soil solution, an air conduit for applying vacuum and positive pressure to the receptacle and a sample transfer conduit for conveying samples from the receptacle, the improvement comprising:
   a porous stainless steel tube forming a sole permeable portion of a wall of the receptacle for permitting transfer of soil solution into the receptacle on application of vacuum to the receptacle.

9. A suction lysimeter comprising:
   a stainless steel receptacle;
   a divider forming first and second chambers in the receptacle;
   a porous stainless steel receptacle wall portion adjacent only the first chamber;
   a sample transfer conduit extending from the second chamber to the exterior of the receptacle;
   a fluid path connecting the two chambers; and
   a one-way check valve in the fluid path permitting flow of soil solution only from the first chamber to the second chamber.

* * * * *